United States Patent [19]

Leonhardt

[11] Patent Number: 5,693,029
[45] Date of Patent: Dec. 2, 1997

[54] PRO-CELL INTRA-CAVITY THERAPEUTIC AGENT DELIVERY DEVICE

[75] Inventor: Howard J. Leonhardt, Davie, Fla.

[73] Assignee: World Medical Manufacturing Corporation, Sunrise, Fla.

[21] Appl. No.: 500,419

[22] Filed: Jul. 10, 1995

[51] Int. Cl.⁶ ............................................. A61M 25/00
[52] U.S. Cl. ............................................. 604/264; 604/280
[58] Field of Search ............................ 606/192, 194; 604/93, 96, 97, 98, 99, 100, 101, 102, 103, 280, 264, 46

[56] References Cited

U.S. PATENT DOCUMENTS

| | | | |
|---|---|---|---|
| 4,861,336 | 8/1989 | Helzel | 604/95 |
| 5,088,979 | 2/1992 | Filipi et al. | 604/26 |
| 5,112,305 | 5/1992 | Barath | 604/96 |
| 5,196,024 | 3/1993 | Barath | 606/159 |
| 5,252,159 | 10/1993 | Arney | 156/169 |
| 5,304,121 | 4/1994 | Sahatjian | 604/53 |
| 5,320,634 | 6/1994 | Vigil et al. | 606/159 |
| 5,324,260 | 6/1994 | O'Neill et al. | 604/96 |
| 5,354,279 | 10/1994 | Hofling | 604/164 |
| 5,389,314 | 2/1995 | Wang | 264/25 |
| 5,415,637 | 5/1995 | Khosravi | 604/105 |
| 5,419,777 | 5/1995 | Hofling | 604/264 |
| 5,464,395 | 11/1995 | Faxon et al. | 604/96 |
| 5,538,504 | 7/1996 | Linden et al. | 604/53 |

*Primary Examiner*—Corrine M. McDermott
*Assistant Examiner*—Deborah B. Blyveis
*Attorney, Agent, or Firm*—Paul F. Bawel

[57] ABSTRACT

A flexible and kink-proof intra-cavity delivery catheter for precise placement and injection of therapeutic agent(s) into and/or through the wall of a body cavity at a precise treatment site with even distribution throughout. One or more needle assemblies are disposed around a calibrated balloon which, when inflated, brings each needle assembly into contact with and enables the piercing of the cavity wall to a calibrated depth. Each needle assembly consists of a plurality of tissue insertion needles along the longitudinal axis of the needle assembly. Precise amounts of the therapeutic agent are then quickly delivered through the needle assembly directly into the diseased body tissue. When the calibrated balloon is deflated, retraction members pull the needle assemblies back into the catheter body for catheter repositioning or catheter withdrawal. The problems of over-treatment and undertreatment of the treatment site and the body with therapeutic agents, uneven distribution of therapeutic agents within the diseased treatment site, additional trauma to the treatment site, and long term blockage of body fluid distal to the treatment site via known drug delivery catheters are thereby eliminated.

17 Claims, 3 Drawing Sheets

PRO-CELL INTRA-CAVITY THERAPEUTIC AGENT DELIVERY DEVICE

FIELD OF THE INVENTION

This invention relates to catheters, specifically to a new catheter for delivering therapeutic agents to body cavity walls, such as blood vessels.

BACKGROUND OF THE INVENTION

PRIOR ART

Atherosclortic Cardiovascular Disease (ACD) and Peripheral Vascular Disease (PVD) cause the death of many people in industrialized nations. As a result of both diseases, an occlusive lesion forms on the vessel(s) involved, and this lesion is called a thrombus. A thrombus is an aggregate of elements formed on the wall of the involved vessel(s) from components of the blood in response to a thrombogenic stimuli, and is called thrombosis. Blood flow distal to the thrombosis is reduced, and left untreated eventually results in damage to body tissue nourished by blood flow from the diseased vessel(s).

Historically, Coronary Artery By-Pass Grafting (CABG) has been the preferred treatment of thrombosis involving heart arteries. Less invasive treatments exist and maintain a substantive percentage of the procedures performed to battle these diseases. However, CABG remains the most effective long-term treatment for most patients, and is therefore the treatment generally employed by treating physicians, regardless of the excessively increased danger involved with CABG relative to other treatments by catheters and medications.

Balloon angioplasty is a treatment method by which an expandable deflated balloon is introduced via a catheter into the diseased artery and placed along the occlusion. The balloon is then inflated, thereby opening the vessel to its healthy passage diameter. However, almost one-half of the patients treated by this method have thrombosis reoccurrence to some degree through a vascular process known as restenosis. Almost one-third of all patients treated with balloon angioplasty require one or more treatments some time soon after the first angioplasty because of restenosis.

Scientist believe restenosis is caused by damage to the interior layers of the vessel wall, and exposure of these layers to the blood from splitting of the endothelium and intima layers of the vessel. The resulting damage exposes and traumatizes the smooth muscle cells of the vessel wall. In response, the vessel wall calls on the body to repair itself. The result is the production of an excessive amount of the smooth muscle cells, thereby causing the ensuing restenosis.

Preventing the restenosis is a major goal of many scientists. The preferred treatment for the restenosis is to medicate the treatment site with agents known to prevent smooth muscle cell growth. But many of these agents are toxic to humans at the levels necessary to prevent growth by methods now known and available, because with current delivery devices the entire body must be medicated to a level sufficient to deposit an appropriate amount of the therapeutic agent at the treatment site for absorption by the tissue. Furthermore, it is generally not advantageous to medicate the entire body for the purpose of treating a small site, even with non-toxic agents.

Currently, some devices exist which provide for the localized treatment of sites within body cavities. Many of these place the treatment device containing the treating agent in contact with the cavity wall at the site to be treated, and simply release the agent onto the wall of the cavity. Such devices are disclosed in Arney U.S. Pat. No. 5,252,159, Wang U.S. Pat. No. 5,389,314, and Khosravi U.S. Pat. No. 5,415,637. Whereas the agent is received at the treatment site, most of the agent is washed away by moving body fluids resulting in unnecessary treatment of the rest of the body, inadequate treatment of the diseased site, or both. With other of these devices, the agent is coated on the outside of the treatment device and begins dissolving into the body as soon as the device is introduced therein, prior to reaching the treatment site. All of these types of devices require the occlusion of the blood vessel when treating thrombosis for an extended period of time for the medication to be exposed to the tissue for a sufficient amount of time.

Other devices force the agent into the cavity wall through openings in the device which are in contact with the cavity wall. Some of these devices require long exposure because the agent is introduced at low pressure, resulting in partial delivery of the agent into the wall with the rest of the dispensed agent being dispersed throughout the body; the device is ineffective for the treatment of coronary arteries because of the blockage of the blood supply distal to the site. Barath U.S. Pat. No. 5,112,305 is a device which "jets" the agent into the wall, resulting in further damage and trauma from multiple puncture wounds from the jets, and risks puncturing through the entire vessel wall with potentially dangerous results. Also, a portion of the agent is lost into the cavity from spillage during and leakage after the treatment, again resulting in an imprecise treatment of the site and unnecessary treatment of the rest of the body.

Hofling U.S. Pat. No. 5,354,279 and Hofling U.S. Pat. No. 5,419,777 each provide for the injection of an agent into the cavity wall with one or more individual needles, where each needle requires a separate lumen to be deployed from the catheter. However, it is extremely difficult, if not impossible to determine the depth of penetration of the needles into the wall because the device must be manipulated prior to introduction into the body, and a minute change in the difficult setup results in needle penetration at different rates for each needle. Also, penetration is dependent upon the skill of the administrator, and there is no calibration system allowing for a certain penetration depth relative to a certain device manipulation by the administrator. This device allows for only an estimated depth prior to treatment, the actual depth being on a "hit or miss" method attempted during the invasive procedure. This device requires a rigid head at the tip of the catheter which limits the use of the device in torturous severely bending vessels requiring continuous non-kinking flexibility.

This same device does not allow for uniform delivery of the therapeutic agent throughout the diseased site, because the configuration of the device allows for needle placement for each delivery cycle to be administered only in a cross-sectional plane normal to the blood flow through the vessel, such as one might imagine from the tips of an opened umbrella. The average length of an atherosclerotic lesion is between twenty (20) to thirty (30) millimeters. Therefore, this device must be manually repositioned several times within the vessel along the treatment site, and the drug delivery cycle must be repeated several times to approximate a uniform delivery of the agent at imprecise and varying depths into the vessel wall. If the vessel is small, the device will only house a single needle requiring even more drug delivery cycles, greatly increasing the problems listed above and restricting blood flow distal to the device.

The need remains, therefore, for an easily employed and precise method and device allowing for the fast and efficient delivery of therapeutic agents into and/or through multiple points of the cavity walls at a calibrated depth, which will then allow for the administration of a calibrated amount of the desired therapeutic agent(s) to be delivered only to and uniformly along the treatment site; this method and device also allowing for minimal invasion of the cavity wall for a minimal amount of time so as not to further traumatize and damage the treatment site or dependent surrounding/distal tissue.

OBJECTS AND ADVANTAGES

The objects and advantages of the invention are, and the disclosed invention reveals a novel catheter device and method of treatment allowing the delivery of precise amounts of therapeutic agents at the precise site of the diseased tissue, without allowing the agents to disperse distally into the bloodstream; without causing further trauma or damage to the tissue; requiring the device to be resident in the body cavity only for a short period of time; allowing for the quick delivery of therapeutic agent(s) at calibrated depths into or through the cavity wall; delivering the therapeutic agent(s) to multiple points along the length of the atherosclerotic lesion or treatment site during a single drug delivery cycle at said calibrated depths, even in small arteries where there is only one lumen available for a needle assembly; and uniformly distributing the therapeutic agents throughout the diseased tissue with minimal operator manipulation of the device from a single or minimal delivery cycles.

A BRIEF DESCRIPTION OF THE DRAWINGS

DESCRIPTION OF INVENTION

Figure 1:
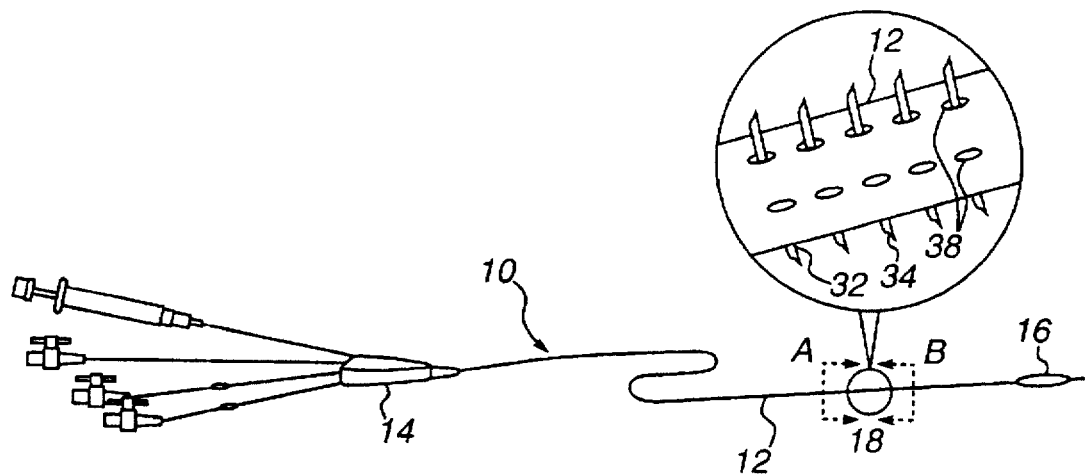
FIG. 1 shows one embodiment of the invention in its engaged position relative to an entire catheter configuration.

The desired embodiment, as shown in FIG. 1 incorporates a catheter 10 which may be inserted into a body cavity in a well-known manner. The catheter includes an catheter body 12, a proximal backend 14, and an angioplasty balloon or distal balloon 16 of the type commonly use in the art at the catheter's 10 distal end. The invention resides internally to the catheter body 12 during the catheter's 10 insertion into the patient. The invention resides close to the distal end of the catheter 10, at the flexible and expandable invention site 18, allowing sufficient space distal to the invention for the angioplasty balloon 16 to reside internally to the catheter body 12 during insertion of the catheter 10 into the patient. Once the angioplasty procedure is completed, the catheter 10 is advanced in the cavity so that the flexible and expandable invention site 18 aligns with the treatment site where the balloon 16 was just employed.

Figure 2:
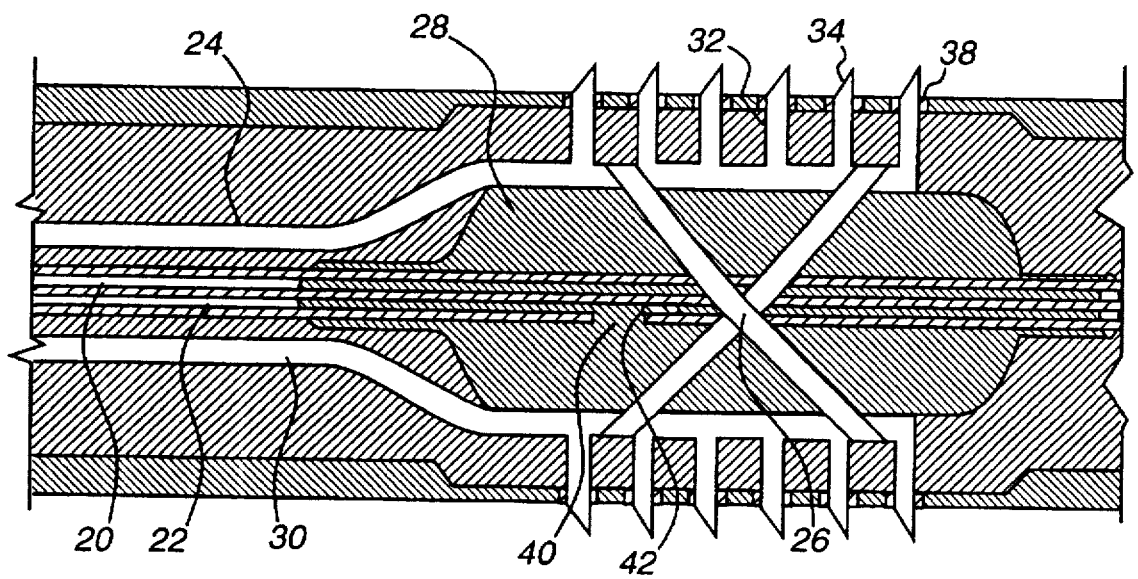
FIG. 2 is a cross-sectional drawing along the longitudinal axis of the invention with the internal inflation balloon in its engaged position; the section shown is between cutting planes A and B shown in FIG. 1.

FIG. 2 shows the flexible and expandable invention site 18, that part of the catheter between cutting planes A and B in FIG. 1, in a cross-sectional view along the longitudinal axis of the flexible and expandable invention site 18. Internally to the catheter body 12, is a distal balloon inflation lumen 20, an internal balloon inflation lumen 22, one or more needle assemblies 24, one or more retraction members 26, and the internal inflation balloon 28. The distal balloon inflation lumen 20 supplies the angioplasty balloon 16 with its expansion agent. The internal balloon inflation lumen 22 also provides the internal inflation balloon 28 with an expansion agent commonly known in the art, which is not shown. The internal inflation balloon 28 is formed around and sealed on the distal balloon inflation lumen 20 and the internal balloon inflation lumen 22 in a manner commonly known in the art at the flexible and expandable invention site 18. The needle assemblies 24 each include a hollow shaft 30, a plurality of tissue insertion needles 32 which also are hollow, and each tissue insertion needle has a tip 34 which is machined so as to easily and efficiently pierce the tissue at the treatment site with negligible trauma and damage. Each tip 34 is open, creating a channel 36 in each needle assembly 24 from the proximal backend 14 end of the needle assembly 24 through the hollow shaft 30, opening into each tissue insertion needle 32 and out through each tip 34. The channel 36 is such that each element of a needle assembly 24 is in fluid communication with all other elements of that needle assembly 24, the only openings being to the outside of the patient at the proximal backend 14 and to the inside of the patient at each tip 34 of that needle assembly 24. The extreme distal end of the hollow shaft 30 of each needle assembly 24 is sealed such that there is no fluid communication of therapeutic agents thereafter. The needle assembly is made of a resilient, flexible, and non-kinking material which resists twisting when torqued, such as nytenol. This allows for rotating the catheter between delivery cycles without withdrawing the catheter from the patient.

The channel 36 is the pathway for depositing treatment agents, such as anti-restenosis drugs and endothelial cells into the treatment site. The needle assembly is also suitable for delivering drugs dispensed in bioadhesive material such as Fibrin glue. The bioadhesive material will not stick to or clot any element of the needle assemblies.

The tissue insertion needles 32 are located at the distal end of the hollow shaft 30, and are essentially perpendicular to the hollow shaft 30. Each needle assembly 24 is positioned within an outer lumen so that the tissue insertion needles 32 are also essentially perpendicular to the length of the catheter 10, and exit the portals 38 essentially normal to the imaginary surface area created by the portals 38. The length of each tissue insertion needle 32 is sufficient to extend through the portals 38 and into or through the cavity wall to a desired calibrated depth when the internal balloon 28 is inflated. The number of tissue insertion needles 32 on each needle assembly 24 is determined by the size of the treatment site and disposition characteristics of the prescribed treatment agent in the tissue. The portals are holes which extend through the catheter body wall into the outer lumens.

When the flexible and expandable invention site 18 is aligned with the treatment site, the operator inflates the internal inflation balloon 28 with an agent commonly known in the art through the internal balloon inflation lumen 22. The internal balloon inflation lumen 22 contains a fill hole 40, and a stopper 42 placed distal to the fill hole 40 and internally to the internal balloon inflation lumen 22. The stopper 42 prevents the inflation agent from passing beyond it, thereby forcing the inflation agent out of the fill hole 40 and into the internal inflation balloon 28. The internal inflation balloon 28 has a calibrated internal volume and expansion rate such that the injection of a known quantity of inflation agent results in a known increase in the outside diameter of the internal inflation balloon 28, thereby allowing the tips 34 of the tissue insertion needles 32 to penetrate the cavity wall to the precise depth desired. The therapeutic agent is then injected into the diseased tissue via the channel 36 in the needle assemblies 24 in a desired amount without leakage or spillage.

Figure 3:
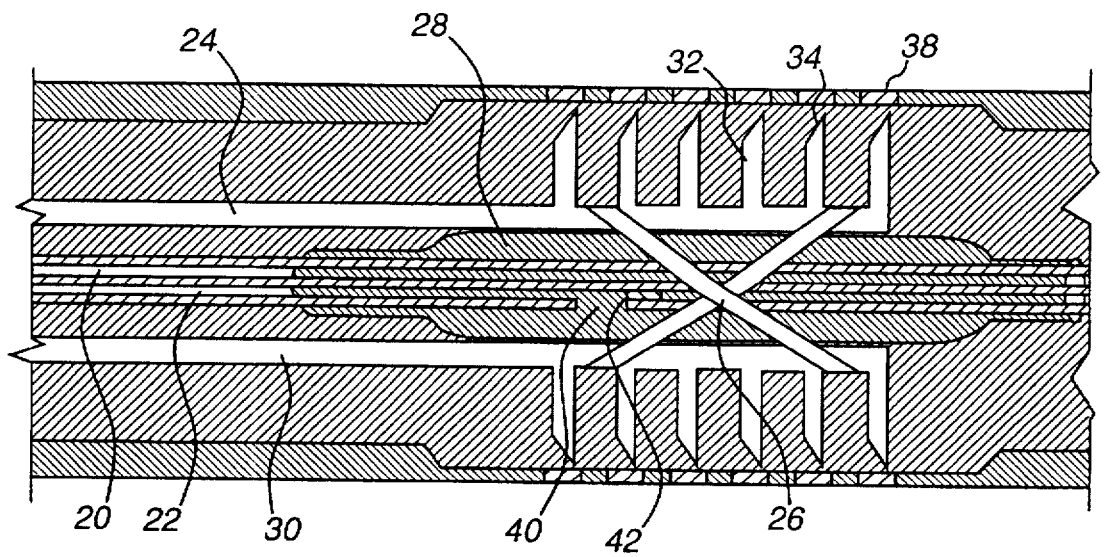
FIG. 3 is the same as FIG. 2 but the invention is in its disengaged position with the balloon deflated; the section shown is between cutting planes A and B shown in FIG. 1.
Figure 4:
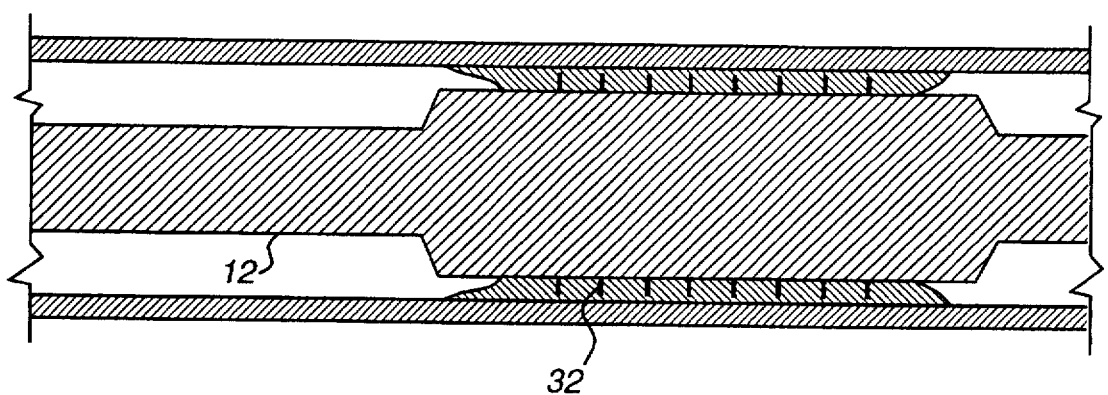
FIG. 4 is a cross-sectional view of the artery along its longitudinal axis showing one embodiment of the invention with the needle assemblies engaged within the treatment site.

Once the therapeutic agent is delivered into the treatment site, (see FIGS. 3 and 4) the inflation agent in the internal inflation balloon 28 is withdrawn through the fill hole 40 and the internal balloon inflation lumen 22, thereby deflating the internal inflation balloon 28. To prevent the tissue insertion needles 34 from becoming stuck in the tissue, the retraction members 26 pull the needle assemblies 24 back into the catheter body 12 so that the tips 34 are not extending through the portals 38. These retraction members 26 are generally an elastic material, such as a rubber band or a locking ring, and are positioned so that they oppose the outward pressure of an inflated internal inflation balloon 28. Each end of the retraction members 26 are placed around a tissue insertion needle 34 of different needle assemblies 24 through access openings (not shown) in the lumens in the vicinity of the flexible and expandable invention site 18. If desired the catheter 10 can be rotated so that another part of the treatment site may be injected with the therapeutic agent, such as may occur in small arteries where only a limited amount of needle assemblies can be configured within the catheter body. However, since the needle assemblies 24 contains multiple tissue insertion needles 32 which extend over the length of the treatment site, it is not necessary to further insert or withdraw the catheter 10 in the artery, as the flexible and expandable invention site 18 is already placed along the entire treatment site. Another reason to rotate the catheter 10 is to inject a different therapeutic agent into the portion of the treatment site just treated. This is possible because each needle assembly 24 may carry a different therapeutic agent from any other needle assembly 24, depending on the type of proximal backend 14 employed.

Inflating the internal inflation balloon, delivering the therapeutic agent or agents to the treatment site, and deflating the internal inflation balloon defines one delivery cycle.

Figure 5:
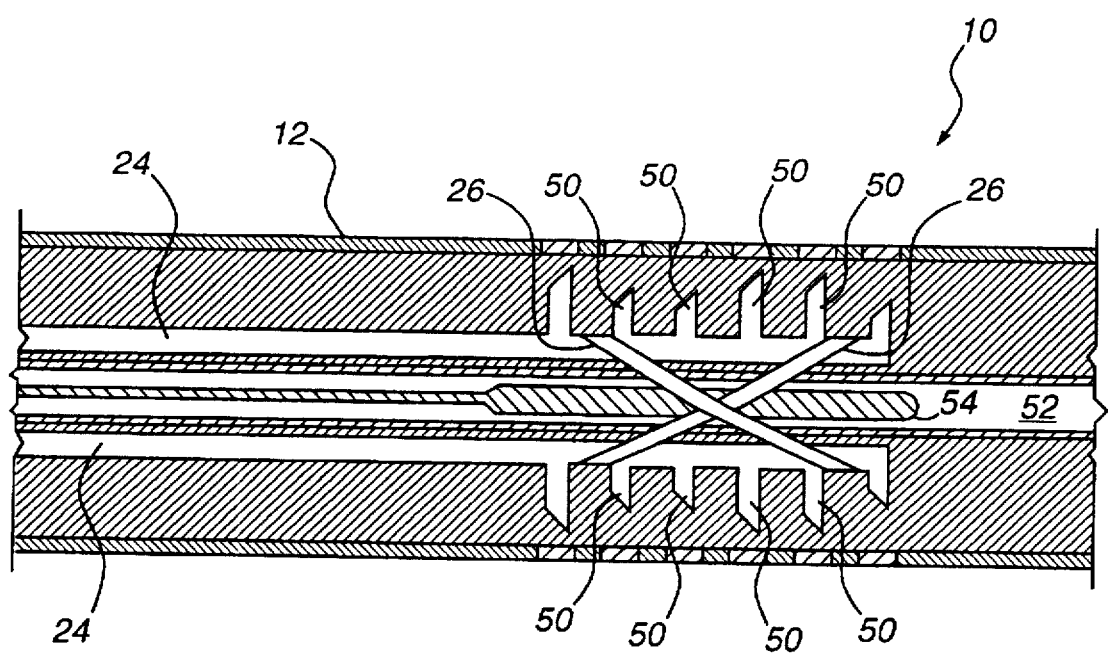
FIG. 5 is a cross-sectional drawing along the longitudinal axis of the invention showing a central lumen and needle assemblies with tissue insertion needles of varying lengths according to the principles of the present invention; the section shown is between cutting planes A and B shown in FIG. 1.

Another embodiment shown in FIG. 5 includes a catheter 10, a catheter body 12, a proximal backend, and a treatment site. The catheter body 12 has internal to it a central lumen 52 extending the entire length of and through the distal end of catheter body 12. The central lumen 52 is surrounded by one or more outer lumens which extend through the catheter body 12 to at least beyond the flexible and expandable invention site 18. It is not necessary for the outer lumens to be opened at the distal end of the catheter body 12, and in fact it may be preferred that they be closed at the distal end of catheter body 12. The outer lumens contain the needle assemblies 24 and have access openings in the vicinity of the flexible and expandable invention site 18 through which the retraction members 26 pass. The retraction members 26 are deployed around the needle assemblies 24 as in the previous embodiment, and are of sufficient size so as not to restrict the internal diameter of the central lumen 52. The central lumen 52 allows for a commonly known guide wire to be employed in a commonly known manner during insertion of the catheter body 12 into the body. Once the catheter body 12 is in position, the guide wire is removed and a commonly known angioplasty balloon is inserted into the central lumen 52 and employed in a commonly known manner to effect the angioplasty procedure. Once the angioplasty procedure is completed, the angioplasty balloon is removed and an internal inflation 54 balloon is inserted into the central lumen 52 and placed at the flexible and expandable invention site 18. The catheter body 12 is positioned so that the flexible and expandable invention site 18 is adjacent to the treatment site either before or after the insertion of the internal inflation balloon 54, but after the angioplasty treatment. The internal inflation balloon 54 is then inflated and deflated in the same manner as in the previous embodiment to attain piercing to a calibrated depth of the tissue insertion needles 50, and the therapeutic agents are injected in precise amounts to the diseased tissue, also as before, while the internal inflation balloon 54 is inflated. After deflation of the internal inflation balloon 54, the catheter body 12 may be rotated for further agent delivery cycles as before or removed with the internal inflation balloon 54 either in place at the flexible and expandable invention site 18 or withdrawn from the catheter body 12.

Another embodiment of the invention also shown in FIG. 5 would entail essentially either of the embodiments described above, but the tissue insertion needles 50 would be of predetermined variable lengths so that during an agent delivery cycle the therapeutic agents would be delivered into the cavity wall at multiple desired depths. This embodiment would be effective for treating layered or thick cavity walls, or cavity walls and the surrounding tissue outside the cavity wall with one device.

Another embodiment (not shown) of the invention would have the needle assemblies configured with the tissue insertion needles running less than or more than the entire length of the treatment site if so desired by the physician.

Another embodiment of the invention (not shown) has the retraction member or members made of an elastic material in the shape of a ring. Each ring retraction member may or may not have an expansion gap in the ring. The ring retraction member(s) encircles the needle assemblies at both or either end of the needle assemblies, and is held in place by a securing device on either the catheter or the needle assemblies. It functions the same as the elastic band retraction members such that when the internal inflation balloon is inflated, the needle assemblies are extended through the portals and pierce the tissue. During this part of the drug delivery cycle, the ring retraction members expand and exert force on the needle assemblies in a direction opposite to the force of the internal inflation balloon just as the elastic retraction members do. When the internal inflation balloon is deflated, the ring retraction members return to their relaxed state, drawing the needle assemblies completely back into the catheter body.

Whereas the invention has been illustrated and described in detail in the drawings and foregoing descriptions, the same is to be considered as illustrative and not restrictive in character, it being understood that only the preferred embodiment and some alternatives have been shown and described and that all changes and modifications that come within the spirit of the invention are desired to be protected.

What is claimed is as follows:

1. A catheter device and a system useful in the treatment of internal body cavity walls such as blood vessels, said catheter comprising:

a catheter body having a first inner lumen, a second inner lumen, and one or more outer lumens, a proximal backend, and a distal end, said first inner lumen, said second inner lumen and said outer lumens extending from said proximal backend to said distal end;

said first inner lumen existing for the introduction of a guide wire, catheterization balloon, light source, or other device;

an expandable and flexible invention site located close to said distal end of said catheter body comprising one or more needle assemblies each located within one of said outer lumens, an internal inflation balloon in fluid communication with said second lumen and circumferentially surrounding and sealed to said first inner lumen and said second inner lumen such that an internal void is formed within said internal inflation balloon, one or more retraction members encircling said needle assemblies, and portals;

said outer lumens circumferentially surrounding said first inner lumen, said second inner lumen and said internal inflation balloon;

said second inner lumen having a fill hole and a stopper or seal, said fill hole located within said internal inflation balloon, said stopper sealing said second inner lumen distal to said fill hole;

said needle assemblies each comprising a hollow shaft having an open proximal end and a sealed distal end, further having a plurality of tissue insertion needles, said tissue insertion needles and said hollow shaft residing entirely within one of said outer lumens when said internal inflation balloon is deflated, said tissue insertion needles each having a tip with an opening, said tips aligned with said portals;

said hollow shaft, said tissue insertion needles and said tips are sealingly connected and in fluid communication such that therapeutic agents can be transferred from said proximal end of said hollow shaft and out of said open tips of said tissue insertion needles;

said portals extending through said catheter body and into said outer lumens, circumferentially surrounding said internal inflation balloon;

said retraction members are for drawing said tissue insertion needles back into said catheter body;

said inner inflation balloon having a known and calibrated inflation rate and said tissue insertion needles having a known and calibrated length such that inflation of said internal inflation balloon causes said tips of said tissue insertion needles to extend through said portals and pierce the body tissue at a desired treatment site to a known and calibrated depth for the delivery of desired therapeutic agents.

2. A Catheter according to claim 1, wherein said plurality of tissue insertion needles are all of the same calibrated and known length.

3. A Catheter according to claim 1, wherein said plurality of tissue insertion needles are of calibrated and known different lengths.

4. A Catheter according to claim 1, wherein said needle assemblies are flexible and kink resistant.

5. A Catheter according to claim 1, wherein said invention site has a distal end; said needle assemblies extend from said proximal backend of said catheter body to said distal end of said invention site.

6. A Catheter according to claim 1, wherein said needle assemblies have a proximal end and said invention site has a distal end;

said proximal end of each of said needle assemblies extend from a point within said catheter body located distal to said proximal backend and proximal to said invention site, to said distal end of said invention site;

said proximal end of each of one or more of said needle assemblies forming a leak-proof joint with one of said outer lumens;

said outer lumen being in fluid communication with said needle assembly through said leak-proof joint.

7. A catheter device and a system useful in the treatment of internal body cavity walls such as blood vessels, said catheter comprising:

a catheter body having a first inner lumen, and one or more outer lumens, a proximal backend, and a distal end, said first inner lumen and said outer lumens extending from said proximal backend to said distal end;

an internal inflation balloon and an expandable and flexible invention site, said internal inflation balloon positioned within said inner lumen along said expandable and flexible invention site during a delivery cycle, said first inner lumen also existing for the introduction of a guide wire, catheterization balloon, light source, or other device;

said expandable and flexible invention site located close to said distal end of said catheter body comprising one or more needle assemblies each located within one of said outer lumens, one or more retraction members encircling said needle assemblies, and portals;

said first inner lumen surrounded circumferentially by said outer lumens;

said needle assemblies each comprising a hollow shaft having an open proximal end and a sealed distal end, further having a plurality of tissue insertion needles, said tissue insertion needles and said hollow shaft residing entirely within one of said outer lumens when said internal inflation balloon is deflated, said tissue insertion needles each having a tip with an opening, said tips aligned with said portals;

said hollow shaft, said tissue insertion needles and said tips are sealingly connected and in fluid communication such that therapeutic agents can be transferred from said proximal end of said hollow shaft and out of said tips of said tissue insertion needles;

said retraction members are for drawing said tissue insertion needles back into said catheter body;

said portals extending through said catheter body and into said outer lumens, circumferentially positioned around said expandable and flexible invention site;

said inner inflation balloon having a known and calibrated inflation rate and said tissue insertion needles having a known and calibrated length such that inflation of said internal inflation balloon causes said tips of said tissue insertion needles to extend through said portals and pierce the body tissue at a desired treatment site to a known and calibrated depth for the delivery of desired therapeutic agents.

8. A Catheter according to claim 7, wherein said plurality of tissue insertion needles are all of the same calibrated and known length.

9. A Catheter according to claim 7, wherein said plurality of tissue insertion needles are of calibrated and known different lengths.

10. A Catheter according to claim 7, wherein said needle assemblies are flexible and kink resistant.

11. A Catheter according to claim 7, wherein said invention site has a distal end; said needle assemblies extend from said proximal backend of said catheter body to said distal end of said invention site.

12. A Catheter according to claim 7, wherein said needle assemblies have a proximal end and said invention site has a distal end;

said proximal end of each of said needle assemblies extend from a point within said catheter body located distal to said proximal backend and proximal to said invention site, to said distal end of said invention site;

said proximal end of each of one or more of said needle assemblies forming a leak-proof joint with one of said outer lumens;

said outer lumen being in fluid communication with said needle assembly through said leak-proof joint.

13. A catheter device useful in the treatment of internal body cavity walls such as blood vessels, said catheter comprising:

a catheter body having one or more lumens each with a proximal opening and portals for providing passage from the outside of a patient to a treatment site within said patient;

an internal lumen adjacent to and surrounded by said one or more lumens;

one or more needle assemblies residing within said one or more lumens for providing fluid communication from outside said patient to said treatment site;

an expander for engaging said one or more needle assemblies with said treatment site through said portals.

14. The catheter device of claim 13, further comprising:

a retractor for retracting said needle assemblies within said one or more lumens.

15. The catheter device of claim 13, wherein:

said one or more needle assemblies have one or more needles for piercing said treatment site.

16. The catheter device of claim 15, wherein:

said one or more needles are of calibrated and known lengths.

17. The catheter device of claim 13, wherein:

said one or more needle assemblies are flexible and kink resistant.

* * * * *